United States Patent [19]

Hung

[11] Patent Number: 5,491,262
[45] Date of Patent: Feb. 13, 1996

[54] BIS{[1-(2-A-2-B)ETHENYL]}[2-$R^2$-4-X-PHENYL-OR 1-(2-$R^2$-4-X-PHENYL)ETHENYL]METHANES

[75] Inventor: William M. Hung, Alpharetta, Ga.

[73] Assignee: Hilton Davis Chemical co., Cincinnatti, Ohio

[21] Appl. No.: 387,547

[22] Filed: Jul. 28, 1989

Related U.S. Application Data

[62] Division of Ser. No. 167,223, Mar. 11, 1988, Pat. No. 4,870,050.

[51] Int. Cl.$^6$ .................. C07C 211/45; C07C 211/54; C07D 209/14
[52] U.S. Cl. .................. 564/330; 546/192; 546/229; 546/232; 546/236; 548/455; 548/547; 564/335
[58] Field of Search ...................... 548/455, 547; 564/330, 335; 546/229, 232, 236, 192

[56] References Cited

U.S. PATENT DOCUMENTS 4,922,020  5/1990  Gregory et al. .................. 564/330

FOREIGN PATENT DOCUMENTS 289122  11/1988  European Pat. Off. .

OTHER PUBLICATIONS

McEwen et al, Chemical Abstracts, vol. 67 (1967) 21799r.
Bordwell et al, Chemical Abstracts, vol. 108 (1988) 186095m.
Uda et al, Chemical Abstracts, vol. 110 (1989) 48526T.
Uda et al, Chemical Abstracts, vol. 111 (1989) 48214k.

*Primary Examiner*—Richard L. Raymond
*Attorney, Agent, or Firm*—Terrence E. Miesle

[57] ABSTRACT

Bis{[1-(2-A-2-B)ethenyl]} [2-$R^2$-4-X-phenyl- or 1-(2-$R^2$-4-X-phenyl) ethenyl]methanes useful as color formers, particularly in transfer imaging, pressure sensitive and thermal-responsive carbonless duplicating systems, are prepared by the interaction of two molecular proportions of the corresponding 1-A-1-B-ethene with the appropriate 2-$R^2$-4-X-phenyl-$(CH=CH)_n$—CHO presence of an acidic catalyst.

9 Claims, No Drawings

BIS{ [ 1-(2-A-2-B)ETHENYL] } [ 2-R²-4-X-PHENYL-OR 1-(2-R²-4-X-PHENYL)ETHENYL] METHANES

This application is a division, of application Ser. No. 167223, filed Mar. 11, 1988, now U.S. Pat. No. 4,870,050.

BACKGROUND OF THE INVENTION

1. (a) Field of the Invention

The invention described herein relates to novel compounds classified in the field of organic chemistry as methanes, useful as color-forming substances, particularly in the art of transfer imaging, pressure-sensitive and thermal responsive carbonless duplicating and electrochromic recording to transfer imaging systems containing said compounds; to pressure-sensitive and thermal responsive carbonless duplicating systems containing said compounds; to electrochromic recording systems containing said compounds; and to a process for preparing said methanes.

2. (b) Information Disclosure Statement

Several classes of organic compounds of widely diverse structural types are known to be useful as colorless precursors for transfer imaging systems. Among the more important classes, there may be named leuco-type dyestuffs such as: phthalides, for example, crystal violet lactone, Malachite green lactone; fluoran, for example, 3-dialkylamino fluoran, 3-dimethylamino-6-methoxyfluoran; phenothiazines, for example, benzoyl leuco methylene blue; Rhodamines, for example, 3-methyl-spiro-dinaphthopyran. The classes of organic compounds listed above also generally find utility in pressure-sensitive and thermal responsive carbonless duplicating systems.

Typical of the transfer imaging systems is the system described in U.S. Pat. No. 4,399,209 which issued Aug. 16, 1983. In this patent a transfer imaging system is disclosed wherein images are formed by image-wise exposing a layer comprising a chromogenic material and pressure rupturable containing as an internal phase, a photosensitive composition. In this system the chromogenic material is encapsulated with the photosensitive compound. Upon exposure to filtered U.V. or blue light in the wavelength range of 380 to 480 nonometer a certain portion of the capsules will harden. The capsules in which the internal phase has remained liquid are ruptured and the chromogenic material is image-wise transferred to a developer or copy sheet where the chromogenic material reacts with a developer to form an image.

Typical of the many commercially accepted pressure-sensitive and thermal-responsive carbonless copy systems are those described in U.S. Pat. Nos. 2,712,507; 2,800,457; 3,041,289; and 4,000,087, which issued Jul. 5, 1955; Jul. 23, 1957; Jun. 26, 1962; and December 28, respectively.

Several classes of organic compounds of widely diverse structural types are known to be useful as colorless precursors for electrochromic recording. Among the more important classes, there may be named leuco-type dyestuffs such as: phthalides, for examples, crystal violet lactone, Malachite green lactone; fluorans, for example, 3-diethylamino-5,7-dimethylfluoran; and indolinobenzospiropyrans, for example, 1,3,3-trimethyl-6-chloro-8'-methoxyindolinobenzospiropyrans. Also utilized as colorless precursors for electrochromic recording, either alone or in admixture with the leuco compounds indicated above, are substances known as redox indicators. The redox indicator which becomes colored in situ in the electrochromic recording process also is generally a leuco compound. Among the type of compounds which are applicable as redox indicators are phenothiazines, for examples, leuco methylene blue and benzoyl leuco methylene blue. Other specific indicators are Leucoethyl Nile Blue, Leucomethyl Capyrl Blue and Leucosafranine T. Typical of the many such electrochromic recording systems taught in the prior art as those described in U.S. Pat. Nos. 3,726,769, 3,871,972, 3,864,684, 4,017,366, 4,133,933, and Re. 29,427 which issued on Apr. 10, 1973, Mar. 18, 1975, Feb. 4, 1975, Apr. 12, 1977, Jan. 9, 1979, and Oct. 4, 1977, respectively. The methods for electrochromic recording taught in the prior art have many variations. Basically, a sheet of paper is coated or treated on one or both sides with a coating formulation containing at least one colorless color-forming (leuco) compound. Electrical current in the selectively applied to the coated side of the paper by some means, for example, a stylus or a printing head to which an electrical potential can be applied. The application of the current causes any electrochromic reaction involving the leuco compound to produce a visible image corresponding to the design traced by the stylus or that of the printing head.

Many of the color formers in the prior art suffer one or more disadvantages such as low tinctorial strength, low resistance to sublimation, low susceptibility to copiability of the color-developed images in standard office copying machines, for example, a xerographic type of copier, poor image stability in the pressence of light, i.e., the product image fades losing intensity or changes to a less acceptable color, and low solubility in common organic solvents. The latter disadvantage requires the use of specialized and expensive solvents in order to obtain microencapsulated solutions of sufficient concentration for use in pressure-sensitive copying systems and transfer imaging systems.

There are no items to date appear to constitute relevant prior art with regard to the instant invention.

SUMMARY OF THE INVENTION

In its composition of matter aspect, the invention relates to certain bis[1-(2-A-2-B)ethenyl] [2-R²-4-N-R-N-R¹-aminophenyl- or 1-(2-R²-4-N-R-N-R¹-aminophenyl)-2-ethenyl] methanes useful in transfer imaging systems, pressure-sensitive and thermal-responsive carbonless duplicating systems and electrochromic recording systems.

In its process aspect, the invention relates to a process for producing bis[1-(2-A-2-B)ethenyl] [2-R²-4-N-R-N-R¹-aminophenyl- or 1-(2-R²-4-N-R-N-R¹-aminophenyl)-2-ethenyl] methanes which comprises interacting one molecular proportion of the corresponding 2-R²-4-N-R-N-R¹-aminophenyl-(CH=CH)$_n$—CHO with two molecular proportions of the corresponding 1-A-1-B-ethene in the presence of an acidic catalyst.

The present invention provides in one of its article of manufacture aspects, a substrate for use in transfer imaging systems comprising a support sheet containing as a color-forming substance a bis[1-(2-A-2-B)ethenyl] [2-R²-4-N-R-N-R¹-aminophenyl)-2-ethenyl]methane.

The present invention provides in the second of its articles of manufacture aspects, a substrate for use in pressure sensitive and thermal-responsive carbonless duplicating systems comprising a support sheet containing as a color-forming substance a bis[1-(2-A-2-B)ethenyl] [2-R²-4-N-R-N-R¹-aminophenyl- or 1-(2-R²-4-N-R-N-R¹-aminophenyl)-2-ethenyl]methane.

The present invention provides in the third of its articles of manufacture aspects, a substrate for use in electrochromic recording-systems comprising a support sheet containing as a color-forming substance a bis [1-(2-A-2-B)ethenyl] [2-R²-4-N-N-R¹-aminophenyl)-2-ethenyl]methane.

DETAILED DESCRIPTION INCLUSIVE OF THE PREFERRED EMBODIMENTS

More specifically, this invention in one of its composition of matter aspect reside in the novel bis[1-(2-A-2-B)ethenyl] [2-R²-4-X-phenyl- or 1-(2-R² 4-X-phenyl)-2-ethenyl]methanes having the formula

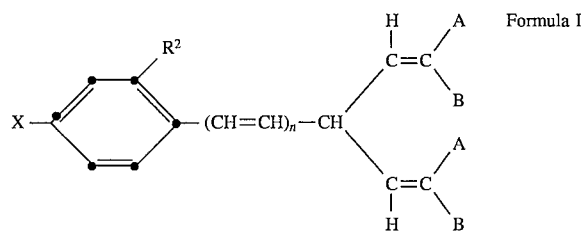

Formula I wherein: A represents a moiety selected from the group consisting of

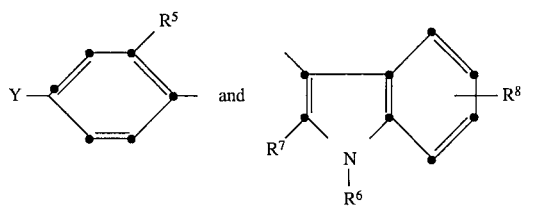

B represents a moiety selected from the group consisting of

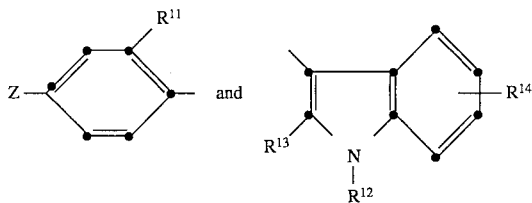

in which X represents hydrogen, N(R)(R¹) or a pyrrolidinyl or piperidinyl; Y represents hydrogen or N(R³)(R⁴); Z represents hydrogen or —N(R⁹)(R¹⁰); wherein R,R³ and R⁹ independently represent hydrogen; non-tertiary $C_1$ to $C_8$ alkyl; benzyl; benzyl substituted in the benzene ring by one or two of non-tertiary $C_1$ to $C_4$ alkyl; non-tertiary $C_1$ to $C_4$ alkoxy, nitro or halo; R¹, R⁴ and R¹⁰ independently represent non-tertiary $C_1$ to $C_8$ alkyl; phenyl; phenyl substituted with one or two of non-tertiary $C_1$ to $C_4$ alkyl, non-tertiary $C_1$ to $C_4$ alkoxy, nitro or halo; benzyl; or benzyl substituted in the benzene ring by one or two of non-tertiary $C_1$ to $C_4$ alkyl, non-tertiary $C_1$ to $C_4$ alkoxy, nitro or halo; R², R⁵ and R¹¹ independently represent hydrogen, non-tertiary $C_1$ to $C_4$ alkyl, non-tertiary $C_1$ to $C_4$ alkoxy, or halo; R⁶ and R¹² independently represent hydrogen; non-tertiary $C_1$ to $C_{16}$ alkyl; or non-tertiary $C_1$ to $C_{16}$ alkyl substituted by non-tertiary $C_1$ to $C_8$ alkoxy, phenoxy, phenyl or phenyl substituted by one or two of non-tertiary $C_1$ to $C_4$ alkoxy, nitro or halo; R⁷ and R¹³ independently represent hydrogen, non-tertiary $C_1$ to $C_4$ alkyl or phenyl; R⁸ and R¹⁴ independently represent one or two of hydrogen, non-tertiary $C_1$ to $C_4$ alkyl, non-tertiary $C_1$ to $C_4$ alkoxy, nitro or halo; and n represents zero or one.

In a first particular embodiment in accordance with its composition of matter aspect, the invention sought to be patented resides in the novel bis 1-[2-(2-R⁵-4-Y-phenyl)-2-(2-R¹¹-4-Z-phenyl) ethenyl] [2-R²-4-X-phenyl- or 1-(2-R²-4-X-phenyl)-2-ethenyl] methanes according to Formula I in which A represent 2-R⁵-4-Y-phenyl and B represents 2-R¹¹-4-Z-phenyl having the formula

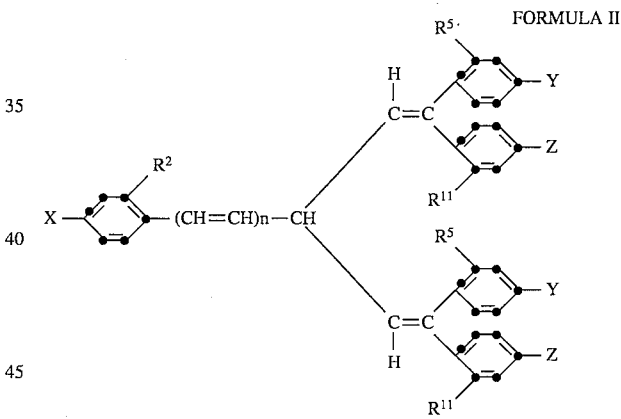

FORMULA II wherein R²,R⁵,R¹¹ X, Y, Z and n have the same respective meanings given in Formula I.

In a second particular embodiment in accordance with its composition of matter aspect, the invention sought to be patented resides in the novel bis {1-[2-(2-R⁵-4-Y-phenyl)-2-(1-R¹²-2-R¹³-5/6-R¹⁴-indol-3-yl)ethenyl]} [2-R²-4-X-phenyl- or 1-(2-R²-4-X-phenyl)-2-ethenyl] methanes according to Formula I in which A represents 2-R⁵-4-Y phenyl and B represents 1-R¹²-2-R¹³-5/6-R¹⁴-indol-3-yl having the formula

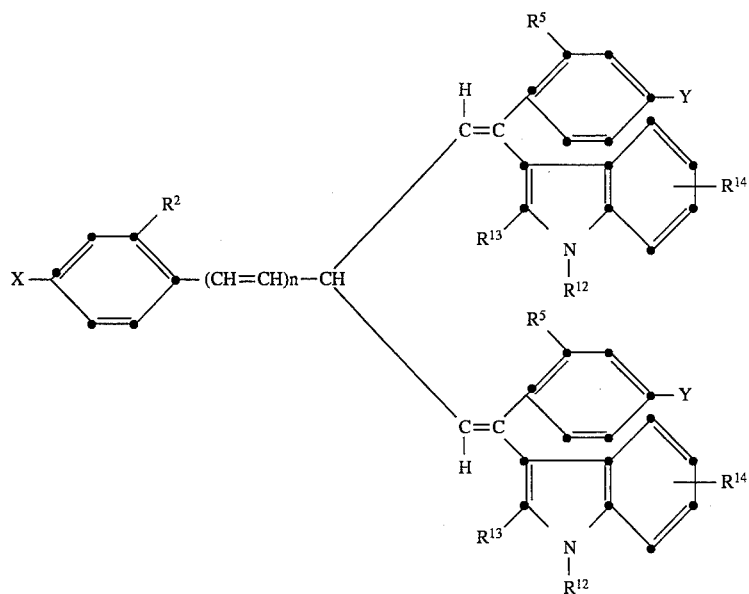

FORMULA III in which $R^2, R^5, R^{12}, R^{13}, R^{14}$, X, Y and n have the same respective meanings given in Formula I.

In a third particular embodiment in accordance with its composition of matter aspect, the invention sought to be patented resides in the novel bis {1-[2-(1-$R^6$-2-$R^7$-5/6-$R^8$-indol-3-yl)-2-(1-$R^{12}$-2-$R^{13}$-5/6-$R^{14}$-indol-3-yl)ethenyl]} [2-$R^2$-4-X-phenyl- or 1-(2-$R^2$-4-X-phenyl)-2-ethenyl] methanes according to Formula I in which A represents 1-$R^6$-2-$R^7$-5/6-$R^8$-indol-3-yl and B represents 1-$R^{12}$-2-$R^{13}$-5/6-$R^{14}$-indol-3-yl having the formula

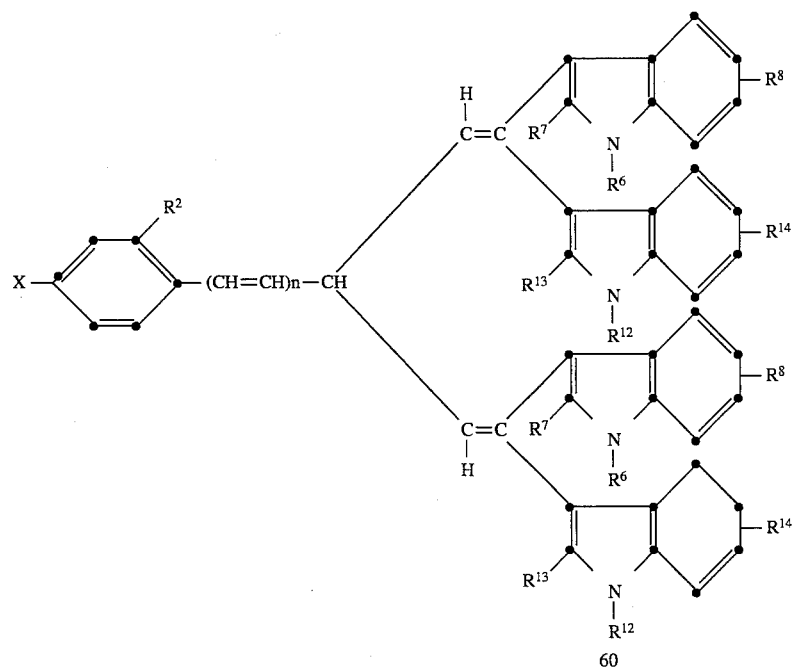

in which $R^2, R^6, R^7, R^8, R^{12}, R^{13}, R^{14}$, X, and n have the same respective meanings given in Formula I.

In its process aspect, the invention sought to be patented resides in the process for preparing a bis [1-(2-A-2-B)ethenyl] [2-$R^2$-4-X-phenyl- or 1-(2-$R^2$-4-X-phenyl)-2-ethenyl] methane according to Formula I which comprises interacting in proportion one molecular of the corresponding aldehyde having the structural formula

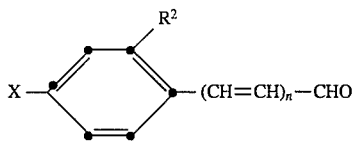

FORMULA V with two molecular proportions of the corresponding 1-A-

FORMULA IV

1-B-ethene having the structural formula

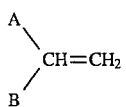

FORMULA VI in the presence of an acidic catalyst in which $R^2$,A,B,X and n have the same respective meanings given in Formula I.

In one of its article of manufacture aspects, the invention sought to be patented resides in a substrate for use in transfer imaging comprising a support sheet coated with a layer containing as a color-forming substance a bis[1-(2-A-2-B)ethenyl] [2-$R^2$-4-X-phenyl- or 1-(2-$R^2$-4-X-phenyl)-2-ethenyl] methane according to Formula 1 wherein A,B,$R^2$,X and n have the same respective meanings given in Formula I.

In a particular embodiment in accordance with its first article of manufacture aspect, the invention sought to be patented resides in a substrate for use in a transfer imaging comprising a support sheet coated with a layer containing as a color-forming substance a bis {1-[2-(2-$R^5$-4-Y-phenyl)-2-(2-$R^{11}$-4-Z phenyl)ethenyl]} [2-$R^2$-4-X-phenyl- or 1-(2-$R^2$-4-X-phenyl- or 1-(2-$R^2$-4-N-R-N-$R^1$-aminophenyl)-2-ethenyl] methanes according to Formula II wherein $R^2$,$R^5$,$R^{11}$ X, Y and Z have the same respective meanings given in Formula II.

In a second particular embodiment in accordance with its first article of manufacture aspect, the invention sought to be patented resides in a substrate for use in transfer imaging comprising a support sheet coated with a layer containing as a color-forming substance a bis {1-[2-(2-$R^5$-4-Y-phenyl)-2-(1-$R^{12}$-2-$R^{13}$-5/6-$R^{14}$ indol-3-yl) ethenyl]} [2-$R^2$-4-X-phenyl- or 1-(2-$R^2$-4-X-phenyl)-2-ethenyl]methane according to Formula III wherein $R^2$,$R^5$,$R^{12}$,$R^{13}$, $R^{14}$,X, and Y have the same respective meanings given in Formula III.

In a third particular embodiment in accordance with its first article of manufacture aspect, the invention sought to be patented resides in a substrate for use in transfer imaging comprising a support sheet coated with a layer containing as a color-forming substance a bis {1-[2-(1-$R^6$-2-$R^7$-5/6-$R^8$-indol-3-yl)-2-(1-$R^{12}$-2-$R^{13}$-5/6-$R^{14}$-indol-3-yl)ethenyl]} [2-$R^2$-4-X-phenyl-or 1-(2-$R^2$-4-X-phenyl)-2-ethenyl} methane according to Formula IV wherein $R^2$,$R^6$,$R^7$,$R^8$,$R^{12}$,$R^{13}$, $R^{14}$, and X have the same respective meanings given in Formula IV.

In a second of its article of manufacture aspects, the invention sought to be patented resides in a substrate for use in a pressure-sensitive and thermal-responsive marking system comprising a support sheet coated with a layer containing as a color-forming substance a bis[1-(2-A-2-B)ethenyl] [2-$R^2$-4-X-phenyl- or 1-(2-$R^2$-4-X-phenyl)-2-ethenyl] methane according to Formula 1 wherein A,B,$R^2$,X and n have the same respective meanings given in Formula I.

In a particular embodiment in accordance with its second article of manufacture aspect, the invention sought to be patented resides in a substrate for use in a pressure-sensitive or a thermal-responsive marking system comprising a support sheet coated with a layer containing as a color-forming substance a bis{1-[2-(2-$R^5$-4-Y-phenyl)-2-(2-$R^{11}$-4-Z-phenyl)ethenyl]}[2-$R^2$-X-phenyl-or 1-(2-$R^2$-X-phenyl-2-ethenyl] methanes according to Formula II wherein $R^2$,$R^5$,$R^{11}$, X, Y and Z have the same respective meanings given in Formula II.

In a second particular embodiment in accordance with its second article of manufacture aspect, the invention sought to be patented resides in a substrate for use in a pressure-sensitive or thermal-responsive marking system comprising a support sheet coated with a layer containing as a color-forming substance a bis{1-[2-(2-$R^5$-4-Y-phenyl)-2-(1-$R^{12}$-2-$R^{13}$-5/6-$R^{14}$ indol-3-yl)ethenyl]}[2-$R^2$-4-X-phenyl- or 1-(2-$R^2$-4-X-phenyl)-2-ethenyl] methane according to Formula III wherein $R^2$,$R^5$,$R^{12}$,$R_R^{13}$14, X and Y have the same respective meanings given in Formula III.

In a third particular embodiment in accordance with its second article of manufacture aspect, the invention sought to be patented resides in a substrate for use in a pressure-sensitive or thermal-responsive marking system comprising a support sheet coated with a layer containing as a color-forming substance a bis{1-[2-(1-$R^6$-2-$R^7$-5/6-$R^8$-indol-3-yl)-2-(1-$R^{12}$-2-$R^{13}$-5/6-$R^{14}$-indol-3-yl)ethenyl]} [2-$R^2$-4-X-phenyl-or 1-(2-$R^2$-4-X-phenyl)-2-ethenyl] methane according to Formula IV wherein $R^2$,$R^6$,$R^7$,$R^8$,$R^{12}$,$R^{13}$, $R^{14}$ and X have the same respective meanings given in Formula IV.

In a fourth particular embodiment in accordance with its second article of manufacture aspects, the invention sought to be patented resides in a pressure-sensitive transfer sheet, adapted for use with a receiving sheet having an electron-accepting layer, comprising a support sheet coated on one side with a layer of pressure-repturable microcapsules, said microcapsules containing a liquid solution of a color-forming substance comprising at least one compound having Formula I.

In a fifth particular embodiment in accordance with its second article of manufacture aspect, resides in a thermal-responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

In the third of its article of manufacture aspects, the invention sought to be patented resides in a substrate for use in electrochromic recording comprising a support sheet coated with a layer containing as a color-forming substance a bis[1-(2-A-2-B)ethenyl]-[2-$R^2$-4-N-R-N-$R^1$ aminophenyl- or 1-(2-$R^2$-4-X phenyl)-2-ethenyl] methanes according to Formula I wherein A,B,$R^1$,$R^2$ and X have the same respective meanings given in Formula I.

In a particular embodiment in accordance with its third article of manufacture aspect, the invention sought to be patented resides in a substrate for use in electrochromic recording comprising a support sheet coated with a layer containing as a color-forming substance a bis{1-[2-(2-$R^5$-4-Y-phenyl)-2-(2-$R^{11}$-Z-phenyl) ethenyl]} [2-$R^2$-4-X-phenyl- or 1-(2-$R^2$-4-X-phenyl)-2-ethenyl] methanes according to Formula II wherein $R^2$,$R^5$,$R^{11}$ X, Y and Z have the same respective meanings given in Formula II.

In a second particular embodiment in accordance with its third article of manufacture aspect, the invention sought to be patented resides in a substrate for use in a electrochromic recording comprising a support sheet coated with a layer containing as a color-forming substance a bis{1-[2-(2-$R^5$-4-Y-phenyl)-2-(1-$R^{12}$-2-$R^{13}$-5/6-$R^{14}$ indol-3-yl)ethenyl]} [2-$R^2$-4-X-phenyl- or 1-(2-$R^2$-4-X-phenyl)-2-ethenyl] methane according to Formula III wherein $R^2$,$R^5$,$R^{12}$,-$R^{13}$, $R^{14}$X and Y have the same respective meanings given in Formula III.

In a third particular embodiment in accordance with its third article of manufacture aspect, the invention sought to be patented resides in a substrate for use in electrochromic recording comprising a support sheet coated with a layer containing as a color-forming substance a bis{1-[2-(1-$R^6$-2-$R^7$-5/6-$R^8$-indol-3-yl)-2-(1-$R^{12}$-2-$R^{13}$-5/6-$R^{14}$-indol-3-yl)ethenyl]} [2-$R^2$-4-X-phenyl-or 1-(2-$R^2$-4-X-phenyl)-2-ethenyl] methane according to Formula IV wherein $R^2$,$R^6$, $R^7$,$R^8$,$R^{12}$,$R^{13}$,$R^{14}$ and X have the same respective meanings given in Formula IV.

As used herein the terms "non-tertiary $C_1$ to $C_8$ alkyl" and "non-tertiary $C_1$ to $C_{16}$ alkyl: denote saturated monovalent straight or branched aliphatic hydrocarbon radicals including methyl ethyl, propyl, isopropyl, butyl, isobuty, amyl, 1-methylbutyl, 3-methylbutyl, hexyl, isohexyl, heptyl, isoheptyl, octyl, isooctyl, n-dodecyl and the like.

The term "non-tertiary $C_1$ to $C_4$ alkoxy" includes saturated acylic, straight or branched-chained groups such as methoxy, ethoxy, propoxy, isopropoxy, butoxy, sec-butoxy and isobutoxy.

As used herein the terms "halo" and "halogen" include chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substitutents are also satisfactory.

The compounds of Formula I hereinabove are essentially colorless in the depicted lactone form. When contacted with a color developer such as those conventionally employed in carbonless duplication systems which are generally acidic in nature, the compounds of Formula I develop brown, blue, navy blue and green-colored images. Illustrative of specific examples of these color developers are clay minerals such as acid clay, active clay, attapulgite and silton clays; organic acids such as tannic acid, gallic acid, propyl gallate and so forth; acid polymers such as phenol-formaldehyde resins, phenol acetylene condensation resins, condensates between an organic carboxylic acid having at least one hydroxy group and formaldehyde, as so forth; metal salts of aromatic carboxylic acids such as zinc salicylate, tin salicylate, zinc 2-hydroxy naphthoate, zinc 3,5-di-tertiary-butyl salicylate, oil soluble metal salts of phenol-formaldehyde novolak resins and so forth. These color developers are also useful in transfer imaging systems. The developed images are very insensitive to light, are of good tinctorial strength, possess excellent xereographic copiability and enhanced solubility in common organic solvents. The compounds are thus highly suitable for use as colorless precursors, that is, color-forming substances in pressure-sensitive carbonless duplicating systems. The compounds of Formula I can be used alone as color formers to product images which are readily copiable, or can be used as toners to admixture with other color formers to produce images of neutral shade which desirably are readily copiable by xerographic means.

The compounds of Formula I may be incorporated into transfer imaging systems which refer to office based systems suitable for making photocopies. One such system is disclosed in U.S. Pat. No. 4,399,209. In this system the color-forming compounds of Formula I are microencapsulated together with a photoinitiator in a photo-sensitive composition in pressure rupturable capsules. The microcapsules are then coated onto a surface of a substrate. Images are formed by image-wise exposing the encapsulated bearing substrate to actinic radiation and rupturing the capsules in the presence of a developer to obtain an image.

The compounds of this invention may be incorporated in any of the commercially-accepted systems known in the carbonless duplicating art. A typical technique for such applications is as follows. Solutions containing one or more colorless compounds of Formula optionally in admixture with other color formers, in suitable solvents are microencapsulated by well-known procedures, for examples, as described in U.S. Pat. Nos. 3,369,649, 3,429,827, and 4,000,087. The microcapsules are coated on the reverse side of a sheet with the aid of a suitable binder and the coated transfer sheet is then assembled in a manifold with the microcapsule coated side in contact with a receiving sheet coated with an electron-accepting substance, for example, silton clay or a phenolic resin. Application of pressure to the manifold such as that exerted by a stylus, typewriter or other form of writing or printing causes the capsules on the reverse side to repture. The solution of the color formers released from the ruptured microcapsules flows to the receiving sheet and on contact with the acidic medium thereon forms brown, blue, navy blue and green-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer, for example, bisphenol A, of the type generally employed in thermal papers such as described in U.S. Pat. No. 3,539,375, that is, papers which produce a colored image when contacted with a heated stylus or heated type in any of the methods generally known in the art.

The compounds of Formula I hereinabove are essentially colorless in the depicted form. When contacted with an electric current from an applied voltage stylus of the type ordinarily employed in electrochromic recording systems, the compounds of Formula I develop brown, blue, navy blue and green-colored images. These developed images are very insensitive to light, that is, once the color is developed, it remains unchanged when subjected to light exposure. The developed images also possess excellent xerographic reproducibility.

The compounds of this invention may be incorporated in any of the commercially-accepted systems known in the electrochromic recording art. Typical techniques for the application of the color formers to paper are well know and are described in numerous patents, for example, U.S. Pat. Nos. Re. 29,427; 3,726,769, 3,864,684; 3,871,972; 3,951,757; 4,017,366; and 4,133,933. The usual paper coatings consist of the color-forming component, an organic metal salt, a binder and some type of conductor, either an inorganic salt or a conductive polymer. This mixture is milled together optionally in the presence of a non-ionic surface active agent until the desired particle size is obtained and then the mixture is coated on paper and dried. Optionally, the color-forming substance can be milled in the presence of a binder and the remaining components milled also in the presence of a binder and the two mixtures combined together prior to coating on paper. Normally the surface of the coated paper is wet with a conductive solution containing an inorganic alkali metal or alkaline earth metal salt; for example, potassium chloride, calcium chloride, sodium chloride, sodium bromide, potassium bromide, potassium nitrate or sodium sulfate immediately prior to the printing with the applied voltage stylus. For a quick qualitative test, it has been determined that the color-forming component can be dissolved is a suitable volatile organic solvent, coated on paper and the coated paper dried to obtain a paper sheet coated with the color-forming component. This coated sheet can then be wet with a conductive salt solution and an image traced with an applied voltage stylus to develop the colored image. A second quick qualitative test which can be utilized to determine the colored image these compounds will produce in electrochromic recording, is to expose paper coated with the compound or a thin layer chromatography plate on which the compound is spotted to bromine vapor which develops the colored image.

The compounds of Formula I can be used alone as color-forming components in electrochromic recording paper or can be used in admixture with one or more other color-forming compounds from the classes consisting of phthalides, for example, Crystal Violet Lactone; fluroans, for example, 3-diethylamine-5,7-dimethylfluoran; redox indicators, for example, phenothiazines such as benzoyl leuco methylene blue and various other type of color-forming components currently employed in commercially-accepted electrochromic recording systems.

The best mode contemplated by the inventors of carrying out this invention will now be described so as to enable any person skilled in the art to which it pertains to make and use the same.

In accordance with one of the aforementioned process aspects of this invention, the compounds of Formula I are obtained by reacting one molecular proportion of a 2-$R^2$-4-N-R-N-$R^1$-aminophenyl-$(CH=CH)_n$ CHO of Formula V with two molecular proportions of a 1-A-1-B-ethene of Formula VI. The reaction is conveniently carried out in an aliphatic alcohol, such as ethanol, isopropanol or 2-ethoxyethanol in the presence of an acidic catalyst, for example, glacial acetic acid or hydrochloric acid at the reflux temperature of the alcohol from approximately twelve hours to approximately seventy-two hour. The methanes of Formula I thus obtained can be isolated by several methods.

One such method is to cool the reaction mixture with an ice-water bath and to collect the methane by filtration. The methane, once isolated, can be purified by conventional means such as recrystallization from a suitable organic liquid and then collected by filtration. Another method of isolation is to pour the reaction mixture into ice water or a mixture of ice and water and dilute aqueous base such as ammonium hydroxide and to filter the methanes from the mixture. An alternative method of isolation is to pour the reaciton mixture into a mixture of water immiscible organic liquid in which the methanes are soluble such as toluene and water or a dilute base such as ammonium hydroxide solution. The organic liquid layer containing the methanes is separated from the aqueous layer and the methane is isolated by removing the organic liquid by evaporation or distillation. The methane, once isolated, can be purified by conventional means such as trituration or recrystallization from a suitable solvent and then collected by filtration. Purification can also be effected by column chromatography. The methane to be purified is dissolved in a suitable organic liquid or combination of organic liquids and the solution is passed through a chromatography column which has been packed with a suitable substrated, for example, silica gel, cellulose, alumina and the like. Numerous fraction are collected and analyzed to determine fraction(s) containing the desired methane. The fraction(s) which contain the desired product are then combined (if more than one) and concentrated to obtain the methane which is then collected by filtration.

Throughout this application the nomenclature 5/6 is used in conjunction with the substitutents in the benzene ring of the indole moiety. This, of course, refers to a substituent in the 5 or 6 position of the benzene portion of the indole moiety or, in the case of two substituents, they are in the 5-and 6-positions.

The molecular structures of the compounds were assigned on the basis of the modes of synthesis and a study of their infrared and nuclear magnetic resonance spectra.

The following examples will further illustrate the invention without, however, limiting it thereto.

EXAMPLE 1

A mixture of 5.7 g of 4-dimethylaminocinnamaldehyde, 16.2 g of 1,1-bis(4-dimethylaminophenyl)ethane, 300.0 ml of ethyl alcohol and 6.0 ml of glacial acetic acid was refluxed approximately eighteen hours. After cooling slightly an additional 3.0 g of 1,1-bis(4-dimethylaminophenyl)ethane was added and reflux maintained for an additional four hours. The resulting reaction mixture was cooled to approximately 5° C. and the solid which formed was collected by filtration. The solid was recrystallized from isopropyl alcohol, filtered and dried to obtain 16.3 g of bis{[2,2-bis(4-dimethylaminophenyl)]ethenyl}[2-(4-dimethylaminophenyl)ethenyl]methane (Formula II: R,$R^1$,$R^3$, $R^4$,$R^9$ and $R^{10}$=$CH_3$; $R^2$, $R^5$ and $R^{11}$=H) a yellow solid which melted at 78°–82° C. Significant infrared maxims appeared at 1610 $cm^{-1}$ (v.s.) and 830 $cm^{-1}$ (v.s.). An acetone solution of the product spotted onto clay, phenolic resin and organic acid coated papers slowly developed a blue-colored image. Exposure of the spotted papers to bromine vapor increased the speed of color development.

EXAMPLE 2

Proceeding in a manner similar to that described in Example 1 above, a mixture 1.5 g of 4-dimethylaminobenzaldehyde, 5.4 g of 1,1-bis(4-dimethylaminophenyl)ethane, 100.0 ml of ethyl alcohol and 2.0 ml of glacial aacetic acid was maintained at reflux approximately forty-two hours. After cooling to ambient temperature, the reaction mixture was poured into one liter of ice water, and the resulting solid was collected by filtration and recrystallized from isopropyl alcohol to obtain 2.5 g of bis{[1,1-bis(4-dimethylaminophenyl)ethenyl]}(4-dimethylaminophenyl)methane, a white solid which melted at 215°–220° C. Significant infrared maxima appeared at 1620 $cm^{-1}$ (v.s.) and 1355 $cm^{-1}$. The nuclear magnetic resonance spectrum was in accord with the assigned structure. An acetone solution of the product spotted onto clay, phenolic resin and organic acid coated papers slowly developed blue-colored images. Exposure of a paper coated with the product to bromine vapor developed a dark blue image. An acetone solution of the product, chloranil and a phenolic resin was coated onto a glass plate and dried. The transmission spectrum of the coating had a significant adsorption at 715 nonometers.

EXAMPLE 3

Following a procedure similar to that described in Example 1 above, 2.5 g of 4-diethylamino-2-methylbenzaldehyde, 5.35 g of 1,1-bis-(4-dimethylaminophenyl)ethane, 50.0 ml of ethyl alcohol and 2.0 ml of glacial acetic acid was heated at reflux for approximately eighteen hours. Two milliliters of concentrated hydrochloric acid was added and reflux continued approximately two hours. After cooling, the reaction mixture was poured onto a mixture of 400.0 ml of ice water, 400.0 ml of toluene and 50.0 ml of concentrated ammonium hydroxide, the resulting mixture was separated and the toluene layer was evaporated to dryness. The residue was recrystallized from hexane to obtain 4.94 g of bis{[1,1-(4-dimethylaminophenyl)ethenyl]}(4-diethylamino-2-methylphenyl)methane, a pale tan solid which melted at 164.5°–166.5° C. The infrared spectrum had significant maxima at 1610 $cm^{-1}$ and 820 $cm^{-cm}$. An acetone solution of the product spotted onto an acidic clay, phenolic resin or an organic acid coated paper slowly developed a turquoise-colored image. Exposure of a paper coated with the product to bromine vapor developed a deep turquoise-colored image.

EXAMPLE 4

Proceeding in a manner similar to that described in Example 3 above, 2.0 g of 4-piperidinylbenzaldehyde, 5.35 g of 1,1-bis(4-dimethylaminophenyl)ethane, 50.0 ml of eithyl alcohol and 2.0 ml of glacial acetic acid were refluxed approximately eighteen hours and 2.0 ml of concentrated hydrochloric acid was added and relux continued for about two hours to obtain after recrystallization from isopropyl alcohol 5.09 g of bis {[1,1-bis(4-dimethylamino phenyl)ethenyl]}(4-piperidinylphenyl) methane, a pale green colored solid which melted at 237°–241.5° C. Significant maxima appeared in the infrared spectrum at 1612 cm$^{-1}$ and 822 cm$^{-1}$. An acetone solution of the product spotted onto an acidic clay, a phenolic resin or an organic acid coated paper slowly develops a blue-green-colored image. A paper coated with he product when exposed to bromine vapor developed a blue colored image.

EXAMPLE 5

With stirring a mixture of 7.5 g of 4-dimethylamino benzaldehyde, 34.2 g of 1,1-bis(ethyl-2-methylindol-3-yl)ethene, 100.0 ml of ethyl alcohol and a few drops of concentrated hydrochloric acid was heated at reflux for approximately eighteen hours. To the reaction mixture there was added 150.0 ml of 2-ethoxyethanol and 100.0 ml of ethyl alcohol was distilled to a pot temperature of 132° C. which was maintained for about four and one half hours. The resulting mixture was poured into a mixture of 1.0 l of ice water, 1.0 l of toluene and 20.0 ml of concentrated ammonium hydroxide. The toluene layer was separated, washed with concentrated aqueous sodium chloride solution and the toluene was evaporated to dryness. Five grams of the residue was dissolved in toluene and the resulting solution was passed through a chromatography column collecting 50.0 ml fractions. After collecting 550.0 ml of elutant the solvent system was switched to three parts toluene and 1 part ethyl acetate. Fractions 16 and 17 were kept, evaporated to dryness and the residue triturated in hexane. The solid which forced was collected by filtration and dried to obtain 1.5 g of bis{[1,1-bis(1-ethyl-2-methylindol-3-yl)ethenyl]}(4-dimethylaminophenyl)- methane, a tan solid which melted over the range 108 to 145° C. The infrared spectrum had significant maxima at 1610 cm$^{-1}$ and 850$^{-cm}$. An acetone solution of the product spotted on to an acidic clay, a phenolic resin and an organic acid slowly develops a dark blue-colored image. An acetone solution of the product, chloranil and Bisphenol A was coated onto a glass plate and dried. The transmission spectrum of the coating had significant adsorption at 690 and 740 nanometers.

EXAMPLE 6

Following the procedure described in Example 5 above, 1.75 g of 4-(dimethylamino) cinnamaldehyde, 12.0 g of 1-(4-dimethyl aminophenyl)-1-(1-octyl-2-methylindol-3-yl)ethene, 100.0 ml of ethyl alcohol and 2.0 ml of glacial acetic acid was heated at reflux for approximately forty hours. The reaction mixture was cooled to a temperature between zero and five degrees. A tarry substance came out of solution and stuck onto the side of the flask. The supernatant liquid was decanted from the flask. The tarry solid was dissolved in toluene and ran through a chromatography column packed with silica gel using 6 parts of toluene and 1 part of ethyl acetate to elute the solution to obtain 6.1 g of 3,3-bis{[1-(4-dimethylaminophenyl)-1-(1-octyl-2-methylindol-3-yl)ethenyl]}{1-(4-dimethylaminophenyl)] prop-1-ene, a brown tarry solid. Significant infrared maxima appeared in the spectrum at 752 cm$^{-1}$ and 1610$^{-cm}$. An acetone solution of the product spotted onto a phenolic resin coated papers develops a green-colored image and when spotted on an acidic clay or an organic acid coated paper develops a navy blue-colored image. An acetone solution of the product, chloranil and Bisphenol A was coated onto a glass plate and dried. The transmission spectrum of the coating had significant adsorption at 715 and 820 nanometers.

EXAMPLE 7

In a procedure similar to that described in Example 5, 1.75 g of 4-(dimethylamino)cinnamaldelyde, 10.0 g of 1-(4-dimethyl aminophenyl)-1-(1-methoxyethyl-2-methylindol-3-yl)ethane, 100.0 ml of ethyl alcohol and 2.0 ml of glacial acetic acid were reacted at reflux temperature for approximately four days. The solids obtained were dissolved in toluene and ran through a chromatography column packed with silica gel using 1 part ethyl acetate and 6 parts toluene to elute saving fractions 5 to 7 to obtain 0.36 g of 3,3-bis{[1-(4-dimethylaminophenyl)-1-(1-methoxyethyl-2-methylindol-3-yl)ethenyl]}[1-(4-dimethylaminophenyl)]prop-1-ene, a yellow solid which melted at 85°–87° C. Significant maxima appeared at 1612 cm$^{-1}$ and 770 cm$^{-1}$ in the infrared spectrum. An acetone solution of the product spotted onto an acid clay coated paper develops a gray-green-colored image, and on a phenolic resin or an organic acid coated paper develops an olive-green-colored image. An acetone solution of the product, chloranil and Bisphenol A was coated onto a glass plate and dried. The transmission spectrum of the coating had significant adsorption at 715 and 815 nanometers.

EXAMPLE 8

Proceeding in a manner similar to that described in Example 5, 1.75 g of 4(dimethylamino)cinnamaldehyde, 6.0 g of 1,1-bis(4-diethylaminophenyl)ethene, 100.0 ml of ethyl alcohol and 2.0 ml of glacial acetic acid was interacted at reflux for approximately twenty-four hours to obtain 2.9 g of 3,3-bis{[1,1-bis(4-diethylaminophenyl)ethenyl]}[1-(4-dimethylaminophenyl)]prop-1-ene, an oil which had significant maxima at 1612$^{cm-1}$ and 828$^{-cm-1}$ in the infrared maxima. An acetone solution of the product spotted onto an acidic clay, a phenolic resin or an organic acid coated paper develops a light blue-green colored image. A paper coated with the product when exposed to bromine vapor develops a dark green-colored image. An acetone solution of the product, chloranil and Bisphenol A was coated onto a glass plate and dried. The transmission spectrum of the coating had a significant adsorption at 845 nanometers.

EXAMPLE 9

Proceeding in a manner similar to that described in Example 5, 1.75 g of 4(dimethylamino)cinnamaldehyde, 5.0 g of 1-(phenyl)-1-(4-dimethylaminophenyl)ethene, 100.0 ml of ethyl alcohol and 2.0 ml of glacial acetic acid were interacted at reflux temperature for approximately three days to obtain 2.59 g of 3,3-bis{[1-(phenyl)-1-(4-dimethylaminophenyl)ethenyl]}[1-(4-dimethylaminophenyl)]prop-1-ene, an oil which had significant maxima at 1612 cm$^{-1}$ and 830 cm$^{-1}$ in the infrared spectrum. An acetone solution of the product spotted onto an acidic clay, a phenolic resin or an organic acid coated paper develops a light brown-colored image. A paper coated with the product exposed to bromine vapor develops a dark brown-colored image. An acetone solution of the product, chloranil and Bisphenol A was coated onto a glass plate and dried. The transmission spectrum of the coating had a significant adsorption at 875 nanometers.

EXAMPLE 10

In a procedure similar to that described in Example 5 above, 2.6 g of cinnamaldehyde, 10.7 g of 1,1-bis(4-dimethylamino phenyl)ethene, 100.0 ml ethyl alcohol and 4.0 ml of glacial acetic acid was interacted approximately eighteen hours at reflux and 2.0 ml of concentrated hydrochloric acid was added and reflux continued for approximately two hours to obtain 2.13 g of 3,3-bis{[1,1-bis(4-dimethyl aminophenyl)ethenyl]}[1-(phenyl)]prop-1-ene, a pale yellow solid which melted at 166°–169° C. Significant maximum appeared at 820 cm$^{-1}$ in the infrared spectrum. An acetone solution of the product spotted onto an acidic clay and a phenolic resin develops a pale blue-colored image and spotted onto an organic acid develops a pale green-colored image.

It is contemplated that by following procedures similar to those described in Examples 1 to 11 above but employing the appropriately substituted 2-R$^2$-4-X-phenyl-(CH=CH)n-CHO with two molecular proportions of the corresponding 1-(2-R$^5$-4-Y-phenyl)-1-(2-R$^{11}$-4-Z-phenyl)ethene there will be obtained the appropriate bis{1-[2-(2-R$^5$-4-Y-phenyl-2-(2-R$^{11}$4-Z-phenyl)ethenyl]}[2-R$^2$-4-X-phenyl- or 1-(2-R$^2$-4-X-phenyl)-2-ethenyl]methanes of Formula II, Examples 12 to 21 presented in Table I hereinbelow.

TABLE I

Bis{1-[2-(2-R$^5$-4-N—R$^3$—N—R$^4$-aminophenyl)-2-(2-R$^{11}$-4-N—R$^9$—N—R$^{10}$-aminophenyl)ethenyl]} [2-R$^2$-4-N—R—N—R$^1$-aminophenyl]methanes of Formula II

| Ex. | n | R | R$^1$ | R$^2$ | R$^3$ | R$^4$ | R$^5$ | R$^9$ | R$^{10}$ | R$^{11}$ |
|---|---|---|---|---|---|---|---|---|---|---|
| 11 | 0 | C$_2$H$_5$ | C$_2$H$_5$ | C$_4$H$_9$O | C$_3$H$_7$ | C$_3$H$_7$ | CH$_3$ | C$_3$H$_7$ | C$_3$H$_7$ | CH$_3$ |
| 12 | 1 | C$_4$H$_9$ | C$_4$H$_9$ | CH$_3$O | C$_2$H$_5$ | C$_2$H$_5$ | OCH$_3$ | C$_2$H$_5$ | C$_2$H$_5$ | OCH$_3$ |
| 13 | 1 | C$_8$H$_{17}$ | C$_8$H$_{17}$ | Cl | C$_4$H$_9$ | C$_4$H$_9$ | Cl | C$_4$H$_9$ | C$_4$H$_9$ | Cl |
| 14 | 0 | C$_3$H$_7$ | C$_3$H$_7$ | C$_2$H$_5$ | C$_8$H$_{17}$ | C$_8$H$_{17}$ | C$_2$H$_5$O | C$_8$H$_{17}$ | C$_8$H$_{17}$ | C$_2$H$_5$O |
| 15 | 1 | C$_6$H$_5$CH$_2$ | C$_6$H$_5$CH$_2$ | CH$_3$ | C$_6$H$_5$CH$_2$ | C$_2$H$_5$ | H | C$_2$H$_5$ | C$_2$H$_5$ | CH$_3$ |
| 16 | 1 | C$_6$H$_5$CH$_2$ | C$_2$H$_5$ | C$_2$H$_5$O | 2,4-(CH$_3$)$_2$C$_6$H$_3$CH$_2$ | H | C$_2$H$_5$ | C$_4$H$_9$ | C$_4$H$_9$ | Cl |
| 17 | 0 | 4-CH$_3$C$_6$H$_4$CH$_2$ | CH$_3$ | Br | C$_6$H$_{13}$ | C$_6$H$_{13}$ | C$_4$H$_9$O | C$_6$H$_{13}$ | C$_6$H$_{13}$ | C$_4$H$_9$O |
| 18 | 0 | 4-ClC$_6$H$_4$CH$_2$ | H | C$_4$H$_9$ | C$_5$H$_{11}$ | C$_5$H$_{11}$ | Br | C$_2$H$_5$ | C$_2$H$_5$ | H |
| 19 | 1 | 3-NO$_2$C$_6$H$_4$CH$_2$ | C$_2$H$_5$ | C$_3$H$_7$O | 4-CH$_3$OC$_6$H$_4$CH$_2$ | CH$_3$ | C$_3$H$_7$ | 4-CH$_3$C$_6$H$_4$CH$_2$ | CH$_3$ | C$_3$H$_7$ |
| 20 | 1 | 2,4-(CH$_3$)$_2$C$_6$H$_3$CH$_2$ | C$_6$H$_{13}$ | CH$_3$O | C$_4$H$_9$ | C$_4$H$_9$ | C$_2$H$_5$O | C$_4$H$_9$ | C$_4$H$_9$ | C$_2$H$_5$O |
| 21 | 1 | Pyrrolidinyl | | H | C$_6$H$_{13}$ | C$_6$H$_{13}$ | CH$_3$ | C$_6$H$_{13}$ | C$_6$H$_{13}$ | CH$_3$ |

It is contemplated that by following procedures similar to those described in Examples 1 to 11 above but employing the appropriately substituted 2-R$^2$-4-X-phenyl-(CH=CH)n—CHO with two molecular proportions of the corresponding 1-(2-R$^5$-4-Y-phenyl)-1-(1-R$^{12}$-2-R$^{13}$-5/6-R$^{14}$-indol-3-yl)ethene there will be obtained the appropriate bis{1-[2-(2-R$^5$-4-Y-phenyl)-2-(1-R$^{12}$-2-R$^{13}$-5/6-R$^{14}$-indol-3-yl)ethenyl]}[2-R$^2$-4-X-phenyl- or 1-(2-4-X-phenyl)- or 1-(2-R$^2$-4-X-phenyl)-2-ethenyl]methanes of Formula III, Examples 22 to 32 presented in Table II hereinbelow.

TABLE II

Bis{1-[2-(2-R$^5$-4-N—R$^3$—N—R$^4$-aminophenyl)-2-(1-R$^{12}$-2-N—R$^{13}$-5/6-R$^{14}$-indol-3-yl)ethenyl]} [2-R$^2$-4-N—R—N—R$^1$-aminophenyl-or 1-(2-R$^2$-4-N—R—N—R$^1$-aminophenyl)-2-ethenyl]methanes of Formula III

| Ex. | n | R | R$^1$ | R$^2$ | R$^3$ | R$^4$ | R$^5$ | R$^{12}$ | R$^{13}$ | R$^{14}$ |
|---|---|---|---|---|---|---|---|---|---|---|
| 22 | 0 | C$_4$H$_9$ | C$_4$H$_9$ | CH$_3$O | C$_2$H$_5$ | C$_2$H$_5$ | CH$_3$ | C$_4$H$_9$ | CH$_3$ | 5-NO$_2$ |
| 23 | 1 | C$_6$H$_{13}$ | C$_6$H$_{13}$ | Cl | C$_6$H$_5$CH$_2$ | C$_6$H$_5$CH$_2$ | H | C$_6$H$_{13}$ | C$_2$H$_5$ | 6-Cl |
| 24 | 0 | C$_8$H$_7$ | C$_8$H$_7$ | H | 4-ClC$_6$H$_4$CH$_2$ | C$_2$H$_5$ | CH$_3$O | CH$_3$OC$_4$H$_8$ | C$_6$H$_5$ | 6-Br |
| 25 | 0 | C$_6$H$_5$CH$_2$ | C$_2$H$_5$ | H | C$_4$H$_9$ | C$_4$H$_9$ | C$_4$H$_9$O | C$_6$H$_5$OC$_4$H$_8$ | C$_3$H$_7$ | 5,6-(CH$_3$)$_2$ |
| 26 | 1 | C$_6$H$_5$CH$_2$ | C$_6$H$_5$CH$_2$ | C$_4$H$_9$O | C$_8$H$_{17}$ | C$_8$H$_{17}$ | C$_2$H$_5$O | 4-CH$_3$C$_6$H$_4$OC$_2$H$_4$ | C$_4$H$_9$ | 5-CH$_3$O |
| 27 | 1 | 4-ClC$_6$H$_5$CH$_2$ | 4-ClC$_6$H$_5$CH$_2$ | CH$_3$ | C$_6$H$_{13}$ | C$_6$H$_{13}$ | H | C$_{16}$H$_{33}$ | C$_2$H$_5$ | 6-CH$_3$O |
| 28 | 0 | C$_5$H$_{11}$ | C$_5$H$_{11}$ | C$_2$H$_5$O | 2,4(CH$_3$)$_2$C$_6$H$_3$CH$_2$ | C$_2$H$_5$ | CH$_3$ | C$_{12}$H$_{25}$ | H | 5-F |
| 29 | 1 | 3-NO$_2$C$_6$H$_4$CH$_2$ | C$_2$H$_5$ | C$_2$H$_5$ | 4-CH$_3$OC$_6$H$_4$CH$_2$ | CH$_3$ | H | 4-CH$_3$C$_6$H$_4$OC$_2$H$_4$ | C$_3$H$_7$ | 5-CH$_3$ |
| 30 | 1 | 2,4-(CH$_3$)$_2$C$_6$H$_3$CH$_2$ | H | CH$_3$O | C$_3$H$_7$ | C$_3$H$_7$ | C$_3$H$_7$O | C$_4$H$_9$OC$_3$H$_6$ | C$_4$H$_9$ | 5-I |
| 31 | 0 | 4-CH$_3$C$_6$H$_4$CH$_2$ | C$_2$H$_5$ | CH$_3$O | 3-NO$_2$C$_6$H$_4$CH$_2$ | H | C$_2$H$_5$ | C$_4$H$_9$ | C$_6$H$_5$ | 6-NO$_2$ |
| 32 | 0 | C$_6$H$_5$CH$_2$ | C$_4$H$_9$ | H | C$_8$H$_{17}$ | C$_8$H$_{17}$ | CH$_3$ | 4-ClC$_6$H$_4$OC$_3$H$_6$ | CH$_3$ | 5-CH$_3$ |

It is contemplated that by following procedures similar to those described in Examples 1 to 11 above but employing the appropriately substituted 2-R$^2$-4-X-phenyl-(CH=CH)n—CHO with two molecular proportions of the corresponding 1-(1-R$^6$-2-R$^7$5/6-R$^8$-indol-3-yl)-1-(1-R$^{12}$-2-R$^{13}$-5/6-R$^{14}$-indol-3-yl)ethene there will be obtained the appropriate bis {1-[2-(1-R$^6$-2-R$^7$-5/6-R$^8$-indol-3-yl)-2-(1-R$^{12}$-2-R$^{13}$-5/6-R$^{14}$-indol-3-yl)ethenyl]}[2-R$^2$4-X-phenyl- or 1-(2-R$^2$-4-X-phenyl)-2-ethenyl] methanes of Formula IV, Examples 33 to 43 presented in Table III hereinbelow.

TABLE III

Bis{1-[2-a-$R^6$-2-$R^7$-5/6-$R^8$-indol-3-yl)-2-(1-$R^{12}$-2-$R^{13}$-5/6-$R^{14}$indol-3-yl)ethenyl]}
2-$R^2$4-N—R—N—$R^1$-aminophenyl- or 1-(2-$R^2$-4-N—R—N—$R^1$-aminophenyl)-2-ethenyl]methanes of Formula IV

| Ex. | n | R | $R^1$ | $R^2$ | $R^6$ | $R^7$ | $R^8$ | $R^{12}$ | $R^{13}$ | $R^{14}$ |
|---|---|---|---|---|---|---|---|---|---|---|
| 33 | 0 | $C_2H_5$ | $C_2H_5$ | $C_4H_9O$ | $C_3H_7$ | H | 5-$NO_2$ | $C_3H_7$ | H | 5-$NO_2$ |
| 34 | 1 | $C_4H_9$ | $C_4H_9$ | $CH_3O$ | $C_4H_9$ | $C_2H_5$ | 6-Cl | $C_4H_9$ | $C_2H_5$ | 6-Cl |
| 35 | 1 | $C_8H_{17}$ | $C_8H_{17}$ | Cl | $C_6H_{13}$ | $C_3H_7$ | 6-Br | $C_6H_{13}$ | $C_3H_7$ | 6-Br |
| 36 | 0 | $C_3H_7$ | $C_3H_7$ | $C_2H_5$ | $C_{16}H_{33}$ | $C_6H_5$ | 5-$CH_3$ | $C_{16}H_{33}$ | $C_6H_5$ | 5-$CH_3$ |
| 37 | 1 | $C_6H_5CH_2$ | $C_6H_5CH_2$ | $CH_3$ | $CH_3OC_3H_6$ | H | 5,6-$(CH_3)_2$ | $CH_3OC_3H_6$ | H | 5,6-$(CH_3)_2$ |
| 38 | 1 | $C_6H_5CH_2$ | $C_2H_5$ | $C_2H_5O$ | $C_6H_5OC_2H_4$ | $C_6H_5$ | 5-$CH_3O$ | $C_6H_5OC_2H_4$ | $C_6H_5$ | 5-$CH_3O$ |
| 39 | 0 | 4-$CH_3C_6H_4CH_2$ | $CH_3$ | $CH_3$ | 4-$CH_3C_6H_4OC_2H_4$ | $C_4H_9$ | 5,6-$(CH_3O_2)$ | $C_2H_5$ | $CH_3$ | H |
| 40 | 0 | 4-$ClC_6H_4CH_2$ | H | $C_2H_5$ | $C_{12}H_{25}$ | $C_2H_5$ | 6-Br | $C_4H_9$ | $CH_3$ | H |
| 41 | 1 | 3-$NO_2C_6H_4CH_2$ | $C_2H_5$ | Br | $C_{10}H_{21}$ | H | 5-F | $C_8H_{17}$ | $C_2H_5$ | 6-$CH_3O$ |
| 42 | 1 | 2,4-$(CH_3)_2C_6H_3CH_2$ | $C_6H_{13}$ | $C_4H_9$ | $C_4H_9OC_4H_8$ | $C_3H_7$ | 6-$CH_3$ | $C_6H_{13}$ | H | 5-$CH_3$ |
| 43 | 1 | Pyrrolidinyl | | H | $C_{14}H_{29}$ | $C_4H_9$ | 6-$CH_3O$ | $C_{14}H_{29}$ | $C_4H_9$ | 6-$CH_3O$ |

EXAMPLE 44

The use of compounds of Formulas II, III, and IV, described in the foregoing examples, as color-forming components in pressure-sensitive microencapsulated copying systems is illustrated by the incorporation and testing of the compounds of Example I, bis{[2,2-bis-(4-dimethylamino phenyl)]ethenyl}[2-(4-dimethylaminophenyl)ethenyl]methane in a pressure-sensitive marking paper. The test paper was prepared by a procedure similar to that described in U.S. Pat. No. 4,275,905.

A. A mixture of 7.8 g of 10 percent aqueous EMA 31 (ethylene maleic anhydride copolymer with a molecular weight range of 75,000 to 90,000, supplied by Monsanto Chemical Co.), 14.5 g of 10 percent aqueous EMA 1104 (ethylene maleic anhydride copolymer with a molecular weight range of 5,000 to 7,000, supplied by Monsanto Chemical Co.), 78.0 ml of distilled water was adjusted to pH 4.0 with the addition of 25 percent aqueous sodium hydroxide. A solution was prepared by dissolving 0.35 g bis{[2,2-bis-(4-dimethylaminophenyl]ethenyl}[2-(4-dimethlyamino phenyl)ethenyl]methane, 0.7 g of 2-(2,4-dimethylphenylamino-3-methyl-6-methyl-6-diethylaminofluoran and 0.15 g of 3,3-bis(1-butyl-2-methylindol-3-yl) in 58.8 g of an alkylbenzene. This solution was added to the aqueous mixture and the resulting mixture was emulsified using a variable speed one-half horsepower Eppenbach Homomixer (Gifford Wood Co., Hudson, N.Y.) at an applied voltage of 60 volts until droplets are smaller than 5 microns. While maintaining the rapid agitation, 22.5 g of 50 percent aqueous Resimene 714 (methylated methylol melamine resin, supplied by Monsanto Chemical Co.) was added over approximately three to five minutes. After the microcapsules had formed, the suspension was transferred to a round bottom flask equipped with a conventional blade-type laboratory agitator and stirred approximately two hours at 50° C. The mixture was then stirred overnight at ambient temperature. The mixture was adjusted to pH 7.0 with the addition concentrated aqueous sodium hydroxide. A.

The microcapsule suspension prepared in part A above was coated on paper sheets to a thickness of approximately 0.0015 inch and the coated sheets of paper air dried. The paper thus coated with the micro-encapsulated colorless precursor was assembled as the top sheet in a manifold system by positioning the coated side in contact with a color developer of the electron-accepting type. More specifically, papers coated with a phenolic resin, organic and or with an acidic clay were employed in this test. An image was then drawn with a stylus on the top sheet bearing the microencapsulated colorless precursor on its reverse side causing the effected microcapsules to rupture thus allowing the solution of the colorless precursor held by said microcapsules to flow into contact with the color-developing substance on the receiving sheet whereupon a color image immediately formed. On the acidic clay receiving sheet the image was a red-black color. On the phenolic resin receiving sheet the image was brown-black. On one organic acid receiving sheet the image was a black color. Both developed images exhibited excellent light stability and near infrared absorption at 775 nm.

EXAMPLE 45

The utility of the compounds of Formulas II, III and IV as color-forming components in thermal marking systems is illustrated by the incorporation and testing of the compound of Example 1, bis{[2,2-bis-(4-dimethylaminophenyl)]ethenyl}[2-(4-dimethylaminophenyl)ethenyl] methane in a thermal-responsive marking paper. The test paper was prepared by a procedure similar to that described in the U.S. Pat. No. 3,539,375.

A. A mixture of 2.0 g of bis{[2,2-bis-(4-dimethylaminophenyl)]ethenyl}[2-(4-dimethylaminophenyl)ethenyl] methane, 8.6 g of a 10 percent aqueous solution of polyvinyl alcohol (approximately 99 percent hydrolyzed, 7.1 g of distilled water and 31.6 g of ¹⁄₁₆ inch diameter zirconium grinding beads was charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a 10 percent aqueous polyvinyl alcohol solution (approximately 99 percent hydrolyzed), 18.2 g of water and 221.1 g of ¹⁄₁₆ inch diameter zirconium grinding beads was charged into a container which was placed in a mechanical shaker. After shaking was effected for one hour, the zirconium beads were removed by straining through a No. 40 sieve.

C. A coating composition was prepared by mixing 2.5 g of the slurry from Part A and 22.5 g of the slurry from Part B. The mixture was then uniformly coated on sheets of paper at a thickness of approximately 0.0015 inch and the coated sheets air dried. The coated paper placed on a smooth flat surface with a stylus heated to approximately 152° C. An intense blue-green colored image corresponding to the traced design promptly developed.

What is claimed is:

1. A bis [1-(2-A-2-B)ethenyl][2-R²-4-X-phenyl or 1-(2-R²-4-X-phenyl)-2-ethenyl] methane having the formula

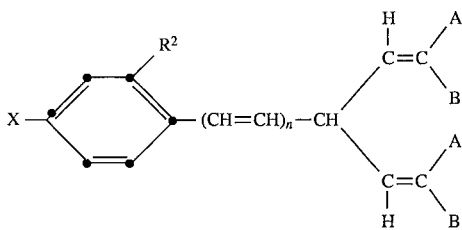

wherein:

A represents a moiety selected from the group consisting of

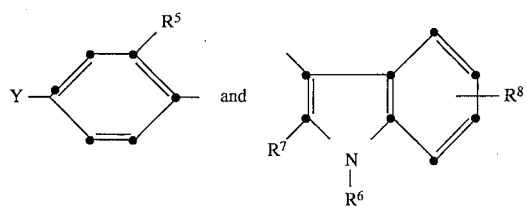

B represents a moiety selected from the group consisting of

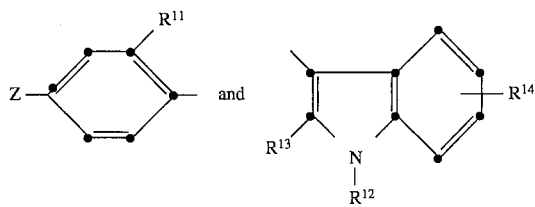

in which X represents hydrogen, —N(R)(R¹), a pyrrolidinyl or piperidinyl; Y represent hydrogen or —N(R³) (R⁴); Z represents hydrogen or —N(R⁹) (R¹⁰) wherein R, R³ and R⁹ independently represent hydrogen; non-tertiary $C_1$ to $C_8$ alkyl; benzyl; or benzyl substituted in the benzene ring by one or two of non-tertiary $C_1$ to $C_4$ alkyl, non-tertiary $C_1$ to $C_4$ alkoxy, nitro or halo; R¹, R⁴ and R¹⁰ independently represent non-tertiary $C_1$ to $C_8$ alkyl; phenyl; phenyl substituted with one or two of non-tertiary $C_1$ to $C_4$ alkyl, non-tertiary $C_1$ to $C_4$ alkoxy, nitro or halo; benzyl; or benzyl substituted in the benzene ring by one or two of non-tertiary $C_1$ to $C_4$ alkyl, non-tertiary $C_1$ to $C_4$ alkoxy, nitro or halo; R², R⁵ and R¹¹ independently represent hydrogen, non-tertiary $C_1$ to $C_4$ alkyl, non-tertiary $C_1$ to $C_4$ alkoxy or halo; R⁶ and R¹² independently represent hydrogen; non-tertiary $C_1$ to $C_{16}$ alkyl substituted by non-tertiary $C_1$ to $C_8$ alkoxy, phenoxy, phenyl or phenyl substituted by one or two of non-tertiary $C_1$ to $C_4$ alkyl, non-tertiary $C_1$ to $C_4$ alkoxy, nitro or halo; R⁷ and R¹³ independently represent hydrogen, non-tertiary $C_1$ to $C_4$ alkyl or phenyl; R⁸ and R¹⁴ independently represent one or two of hydrogen, non-tertiary $C_1$ to $C_4$ alkyl, non-tertiary $C_1$ to $C_4$ alkoxy, nitro or halo; and n represents zero or one with the proviso that only one of X, Y and Z can be hydrogen at the same time.

2. A bis {1-[2-(2-R⁵-4-Y-phenyl)-2-(2-R¹¹-4-Z-phenyl)-ethenyl[}[2-R²-4-X-phenyl or 1-(2-R²-4-X-phenyl)-2-ethenyl]methane according to claim 1 wherein A represents 2-R⁵-4-Y-phenyl and B represents 2-R¹¹-4-Z-phenyl and R², R⁵ and R¹¹ X,Y, and Z have the same respective meanings given in claim 1.

3. A bis {1-[2-(2-R⁵-4-Y-phenyl)-2-(2-R¹²-2-R¹³-5/6-R¹⁴-indol-3-yl)ethenyl]}[2-R²-4-X-phenyl or 1-(2-R²-4-X-phenyl)-2-ethenyl] methane according to claim 1 wherein A represents 2-R⁵-4-Y-phenyl and B represents 1-R¹²-2-R¹³-5/6-R¹⁴-indol-3-yl and R²,R⁵,R¹² R¹³ R¹⁴ X and Y have the same respective meanings given in claim 1.

4. A bis {1-[2-(2-R⁶-2-N-R⁷-5/6-R⁸-indol-3-yl)-2-(1-R¹²-2-R¹³-5/6-R¹⁴-indol-3-yl)ethenyl]}[2-R²-4-X-phenyl- or 1-(2-R²-4-X-phenyl)-2-ethenyl] methane according to claim 1 wherein A is 1-R⁶-2-R⁷-5/6-R⁸-indol-3-yl and B is 1-R¹²-2-R¹³-5/6-R¹⁴-indol-3-yl and R²,R⁶,R⁷,R⁸,R¹²,R¹³, and R¹⁴ and X have the same meanings given in claim 1.

5. A compound of the formula:

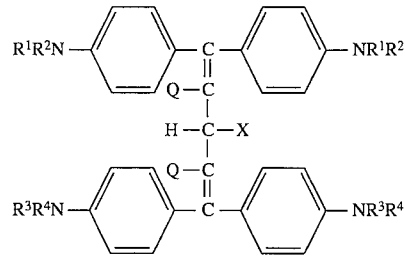

wherein

X is selected from phenyl, and para substituted phenyl, in which the substituent is selected from NR⁷R⁸; and each Q is H;

each R¹ and R² is independently H, $C_{1-4}$-alkyl, trimethylene or $C_{1-4}$alkyl-substituted trimethylene which is also attached to an ortho carbon atom of the adjacent benzene ring;

each R³ and R⁴ is independently H, $C_{1-4}$-alkyl, trimethylene or $C_{1-4}$alkyl-substituted trimethylene which is also attached to an ortho carbon atom of the adjacent benzene ring;

each R⁷ and R⁸ is independently H, aryl, $C_{1-4}$-alkyl, substituted $C_{1-4}$alkyl trimethylene or $C_{1-4}$alkyl-substituted trimethylene which is also attached to an ortho carbon atom of the adjacent benzene ring;

and wherein each benzene ring has no further substitutents.

6. A compound according to claim 5 wherein X is of the formula:

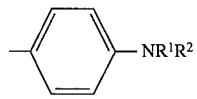

7. A compound according to claim 6 wherein each Q is H, R¹ and R² are methyl or ethyl and R³ and R⁴ are methyl or ethyl.

8. A compound according to claim 7 wherein R⁷ and R⁸ are methyl or ethyl.

9. The compound 1,1,3,5,5-Penta(4-[N,N-dimethylamino]phenyl)-pentadi-1,4-ene.

* * * * *